United States Patent
Hemmings

(10) Patent No.: US 8,141,410 B2
(45) Date of Patent: Mar. 27, 2012

(54) METHOD FOR TESTING PIPETTES

(75) Inventor: Ian Hemmings, Chesterfield (GB)

(73) Assignee: Biohit Oyj, Helsinki (FI)

( * ) Notice: Subject to any disclaimer, the term of this patent is extended or adjusted under 35 U.S.C. 154(b) by 644 days.

(21) Appl. No.: 12/309,922

(22) PCT Filed: Aug. 10, 2007

(86) PCT No.: PCT/FI2007/050442
§ 371 (c)(1),
(2), (4) Date: Feb. 26, 2009

(87) PCT Pub. No.: WO2008/017735
PCT Pub. Date: Feb. 14, 2008

(65) Prior Publication Data
US 2009/0320583 A1 Dec. 31, 2009

(30) Foreign Application Priority Data
Aug. 11, 2006 (EP) .................................. 06397017

(51) Int. Cl.
*G01F 25/00* (2006.01)
(52) U.S. Cl. ........................................... 73/1.74
(58) Field of Classification Search ................ 73/1.74
See application file for complete search history.

(56) References Cited

U.S. PATENT DOCUMENTS

| | | | |
|---|---|---|---|
| 4,790,176 A * | 12/1988 | Marteau d'Autry | 73/1.74 |
| 4,896,270 A | 1/1990 | Kalmakis et al. | |
| 5,465,629 A * | 11/1995 | Waylett, Jr. | 73/864.24 |
| 5,481,900 A | 1/1996 | Husar | |
| 5,492,673 A * | 2/1996 | Curtis et al. | 73/1.74 |
| 7,640,787 B2 * | 1/2010 | Curtis et al. | 73/1.74 |
| 7,976,793 B2 * | 7/2011 | Solotareff et al. | 422/501 |
| 2002/0124627 A1 | 9/2002 | Luchinger | |
| 2006/0096349 A1 * | 5/2006 | Czernecki et al. | 73/1.74 |

FOREIGN PATENT DOCUMENTS

| | | |
|---|---|---|
| EP | 1191312 A2 | 3/2002 |
| WO | WO02/00345 A2 | 1/2002 |

OTHER PUBLICATIONS

"Quick Audit" Internet Citation, (online) Oct. 12, 2004, XP002393677. Retrieved from the Internet: URL:http//web.archive.org/web/http://www.accuteklab.com/quickaudit.html> (retrieved on Aug. 7, 2006), 2 pages.

* cited by examiner

*Primary Examiner* — Thomas P Noland
(74) *Attorney, Agent, or Firm* — Buchanan Ingersoll & Rooney, PC

(57) ABSTRACT

The invention is directed to a method for testing batches of tips for pipettes, the method comprising the steps of calibrating a pipette to be tested with a recommended reference tip, fitting the pipette with a tip to be tested and performing a second calibration and recalibrating the pipette with the reference tip.

9 Claims, No Drawings

METHOD FOR TESTING PIPETTES

FIELD OF THE INVENTION

The present invention is directed to a method of testing batches of tips for pipettes using the same ISO17025 compliant procedures used to UKAS calibrate pipettes.

BACKGROUND OF THE INVENTION

Presently there is no method or service on the market for testing tips for pipettes. Today, tip manufacturers do not batch test their tips on pipettes under carefully controlled conditions such as one would find in, e.g., a UKAS, FINAS, DANAK, NOKAS or OFRAC accredited calibration laboratory.

Much credence is given to the conformity testing and calibration of pipettes. Often the pipetting device is seen in isolation from, perhaps, the two most important variable factors involved in the pipette testing process: the operator and the disposable tip.

With regards to tips, UKAS and the ISO8655 standard treat the pipette and tip as a single device. The certificate obtained in the calibration of a pipette details which type of tip the results were achieved with. This means that this part of the process can be manipulated such that it is not the pipette that is tested but rather the tip being used.

In essence, the question over the accuracy, precision and performance of tips is not one that most pipette users are aware of. Users of pipettes tend towards the assumption that if the tip fits it will work as it should and that any inaccuracy in what they are doing is caused by the pipette as a whole.

SUMMARY OF THE INVENTION

For each pipette make and type there is a recommended tip. The testing method according to the present invention will be able to offer tip conformity testing for any type of tip on a wide range of common pipettes. It would also be possible to conformity specific tips on specific pipette types for a customer.

The invention is directed to a method for testing batches of tips for pipettes, the method comprising the steps of calibrating a pipette to be tested with a recommended reference tip, fitting the pipette with a tip to be tested and performing a second calibration, and recalibrating the pipette with the reference tip. The method is carried out in a UKAS Accredited Calibration Laboratory by a UKAS Authorised Calibrator. The reference pipette is preferably, but not necessarily, a fixed volume pipette.

Under strict UKAS applicable conditions, a reference pipette is fitted with the recommended "reference" tips for that pipette. The pipette is then calibrated according to UKAS and against manufacturers' test specification, with 10 readings taken. In case of a variable volume pipette this is performed over 3 volumes. A UKAS certificate is produced detailing mean volume, inaccuracy and imprecision.

The same pipette is immediately then recalibrated by the same user using the tips under test. No adjustment of the pipette is made to the pipette during this phase. A second UKAS certificate is then produced for the tips under test. Finally the pipette is retested as above using the recommended reference tips, again with no adjustment being made to the pipette. A third UKAS certificate is then produced. This step is performed to ensure that the pipette has not drifted out of calibration since the first calibration run.

Since ISO8655 requires that the tip is changed between dispensings, a minimum of 11 tips are used for a fixed volume pipette and 31 for a variable volume pipette, all of which are from the same numbered batch.

The information from these 3 official UKAS certificates is then summarised. A numerical and optionally a graphical comparison of the three calibration runs is drawn. This makes it easy to see how well the "tip under test" performed compared to the recommended tips and against the manufacturers' specification.

Following the test, the client would be presented with the three UKAS certificates and the certificate of conformity.

Tests have been carried out to determine the validity of the method according to the invention. Preliminary tests have shown, by testing a range of tips, that there is variability between tip makes. The performed tests have clearly shown that the recommended tips performed as expected but that budget generic tips often showed a great variance, which would have actually taken the pipette out of calibration. The variance was shown to originate from the poor quality tips that were causing poor performance, while the pipette was performing according to standards.

The above procedure is an easy method for conformity testing tips. It has shown to be valid in tests and offers a level of quality assurance for end users and manufacturers that has not previously been available. A service offered by the method according to the invention can be offered as an on-site service or as a workshop service.

The invention claimed is:

1. A method for testing batches of tips for pipettes, the method comprising the steps of calibrating a pipette to be tested with a reference tip; fitting the pipette with a tip to be tested and performing a second calibration; and recalibrating the pipette with the reference tip.

2. The method according to claim 1, wherein a certificate is produced detailing mean volume, inaccuracy and imprecision after each of the three steps of calibration of the pipette.

3. The method according to claim 2, wherein the three certificates are compared to each other and a certificate of conformity is produced.

4. The method according to claim 3, wherein the comparison is shown in numerical and/or graphical form.

5. The method according to claim 1, wherein the calibration of the pipette comprises taking more than one reading during each calibration.

6. The method according to claim 5, wherein a minimum of 11 tips are used for a fixed volume pipette and 31 tips are used for variable volume pipettes.

7. The method according to claim 1, wherein the calibration of the pipette comprises taking 10 readings during each calibration.

8. The method according to claim 7, wherein the calibration of a variable volume pipette comprises taking 10 readings over 3 volumes during each calibration.

9. The method according to claim 8, wherein a minimum of 11 tips are used for a fixed volume pipette and 31 tips are used for variable volume pipettes.

* * * * *